US007052649B2

(12) United States Patent
Grossman et al.

(10) Patent No.: US 7,052,649 B2
(45) Date of Patent: May 30, 2006

(54) MERCURY DISPENSER FOR FLUORESCENT LAMPS AND METHOD OF DISPENSING

(75) Inventors: Mark W. Grossman, Belmont, MA (US); William A. George, Lynn, MA (US); Alfred H. Bellows, Wayland, MA (US); Eric Keup, Ipswich, MA (US)

(73) Assignee: Osram Sylvania Inc., Danvers, MA (US)

( * ) Notice: Subject to any disclaimer, the term of this patent is extended or adjusted under 35 U.S.C. 154(b) by 693 days.

(21) Appl. No.: 10/190,260

(22) Filed: Jul. 5, 2002

(65) Prior Publication Data

US 2004/0005241 A1 Jan. 8, 2004

(51) Int. Cl.
*A61L 2/00* (2006.01)

(52) U.S. Cl. .......................... 422/4; 422/123; 422/125; 445/9

(58) Field of Classification Search .................... 422/4, 422/21, 123, 125; 445/9; 220/89.1, 89.2, 220/89.4
See application file for complete search history.

(56) References Cited

U.S. PATENT DOCUMENTS 4,464,133 A * 8/1984 Buhrer .......................... 445/9
5,458,244 A * 10/1995 Emori ......................... 206/527
6,369,503 B1 * 4/2002 Tuttle et al. ................ 313/490
2003/0060798 A1 * 3/2003 Fischer et al. .............. 604/501

* cited by examiner

*Primary Examiner*—John Kim
*Assistant Examiner*—Brad Y. Chin
(74) *Attorney, Agent, or Firm*—William H. McNeill

(57) ABSTRACT

A dispenser (10) for a volatilizable material has a first member (14) that is substantially cup-shaped with a given diameter (X) and with a given depth (Z) and having a first peripheral flange (16) having a first diameter (D). A second member (18) has a second peripheral flange (20) with a second diameter (D2) greater than the given diameter (X). The first peripheral flange (16) and the second peripheral flange (20) are in intimate contact thereby defining a volatilizable material chamber (22) between the bottom (24) of the second member (18) and the bottom (26) of the first cup-shaped member (14). A volatilizable material (12) such as liquid mercury is placed in the chamber; and a hermetic seal (28) is formed between the first and second flanges. When installed in a fluorescent lamp the volatilizable material is released by heating the dispenser with RF current. The material is released when the vapor pressure within the dispenser reaches about 20 atmospheres. For mercury, this pressure is achieved when the dispenser reaches about 600° C.

8 Claims, 4 Drawing Sheets

MERCURY DISPENSER FOR FLUORESCENT LAMPS AND METHOD OF DISPENSING

TECHNICAL FIELD

This invention relates to dispensers for volatilizable materials and more particularly to a dispenser for mercury. Still more particularly, the invention relates to a dispenser for releasing mercury into a desirable environment such as the controlled volume of an arc discharge lamp, in particular, a fluorescent lamp.

BACKGROUND ART

Many arc discharge lamps, including fluorescent lamps, require mercury to function properly. In the past, mercury has been dispensed into fluorescent lamps during processing of the lamps by simply injecting, in one manner or another, a quantity of liquid mercury. Occasionally the mercury has been included in the lamp in the form of an amalgam. Since mercury can be a hazardous substance it would be an advance in the art to develop a system to dispense into a lamp only the necessary amount of mercury. One such system includes a container having the requisite supply of mercury therein, which container is mounted within the fluorescent lamp during processing and subsequently heated to melt a plug within the container, thereby releasing the mercury. Although this system is workable, it has increased cost due to the necessary forming of the escape hole, the solder placement and the cost of the solder. Additionally, the entire cost of the manufacturing is high compared to the present invention.

DISCLOSURE OF INVENTION

It is, therefore, an object of this invention to obviate the disadvantages of the prior art.

It is another object of the invention to enhance the manufacture of arc discharge lamps.

It is yet another object of the invention to provide an economical dispenser of volatilizable materials.

Yet another object of the invention is a method of releasing a volatilizable material into a desired environment in a controlled manner.

These objects are accomplished, in one aspect of the invention, by the provision of a dispenser for a volatilizable material comprising a first member that is substantially cup-shaped having a given diameter and with a given depth and having a first peripheral flange having a first diameter. A second member has a second peripheral flange with a second diameter that is greater than the given diameter and equal to or greater than the first peripheral flange diameter. It is in intimate contact with the first peripheral flange and thereby defines a volatilizable material chamber between the bottom of the second member and the bottom of the first cup-shaped member. A volatilizable material is contained within the chamber; and a hermetic seal is formed between the first and second flanges. The hermetic seal is rupturable when the vapor pressure within the chamber is raised to about 20 atmospheres, thereby releasing the contents. In the case of a chamber containing mercury, this vapor pressure will be reached when the dispenser is heated to about 600° C. If the chamber contains water, the necessary vapor pressure win be reached when the dispenser is heated to about 150° C.

Utilization of the dispenser disclosed herein in the manufacture of fluorescent lamps eliminates virtually any undesired, untimely, contamination by mercury. The capsule is easy to fabricate and relatively inexpensive and is capable of handling mercury (or other material) in doses ranging from 0.15 mg to 30 mg.

BEST MODE FOR CARRYING OUT THE INVENTION

For a better understanding of the present invention, together with other and further objects, advantages and capabilities thereof, reference is made to the following disclosure and appended claims in conjunction with the above-described drawings.

Figure 1:
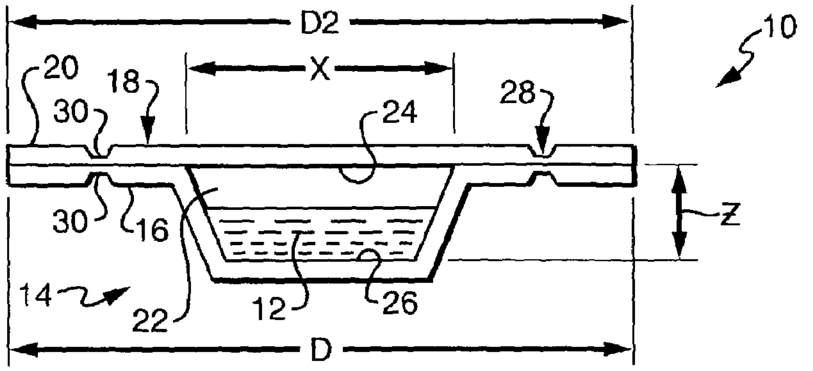
FIG. 1 is a sectional, elevational view of an embodiment of the invention.

Referring now to the drawings with greater particularity, there is shown in FIG. 1 a dispenser 10 for a volatilizable material. The dispenser has a first member 14 that is substantially cup-shaped and has a given diameter X and a given depth Z. A first peripheral flange 16 having a first diameter D extends away from the hollow portion of member 14.

Figure 4:
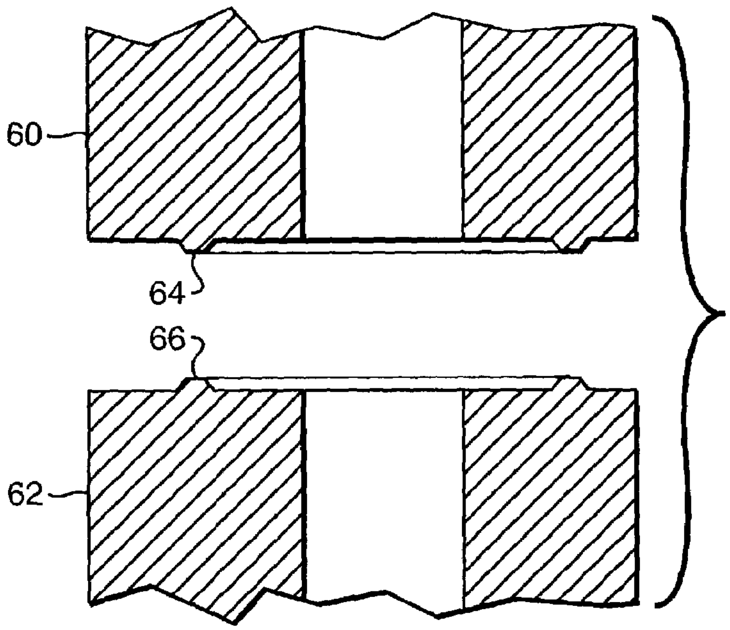
FIG. 4 is an exploded sectional view of the tools employed in making an hermetic seal.

A second member 18 has a second peripheral flange 20 having a second diameter D2 that is greater than the given diameter X. The first peripheral flange 16 and the second peripheral flange 20 are in intimate contact thereby defining a volatilizable material chamber 22 between the bottom 24 of the second member 18 and the bottom 26 of the first cup-shaped member 14. In the embodiment shown in FIG. 1 the second member 18 is essentially a planar disk. A volatilizable material 12 is contained within the chamber 22 and a hermetic seal 28 is formed between the first and second flanges. The hermetic seal 28 comprises a ring seal 30 in the form of a coined annulus. While the ring seal 30 can be formed in only one of the flanges, in a preferred embodiment the ring seal is formed in both the first and second flanges. The rings can be set into the flanges by the tools 60 and 62 shown in FIG. 4, the tools having ring-shaped bosses 64, 66 thereon. If a ring seal 30 is desired in only one flange then one of the tools, for example 62, can have a planar surface. To insure that a hermetic seal is achieved the coining operation is performed at a pressure of 390,000 lbs/in$^2$.

Figure 2:
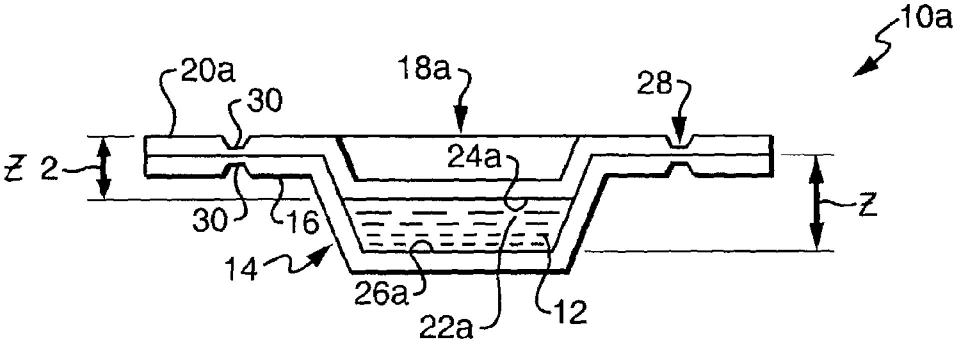
FIG. 2 is a similar view of an alternate embodiment of the invention.

In a second embodiment of the invention, shown in FIG. 2, a dispenser 10*a* for a volatilizable material has a first member 14 that is substantially cup-shaped with a given depth Z and also has a first peripheral flange 16. A second member 18*a* that is substantially cup-shaped and having a second depth Z2 that is less than the first depth Z and having a second peripheral flange 20*a*, is nested within the first member and defines a volatilizable material chamber 22*a* between the bottom 24*a* of the second member and the bottom 26*a* of the first member. The first peripheral flange and the second peripheral flange are in intimate contact.

A volatilizable material 12 is loaded within the chamber and a hermetic seal 28 in the form of a ring seal 30 is formed between the first and second flanges, as in the case of the embodiment shown in FIG. 1.

Figure 3:
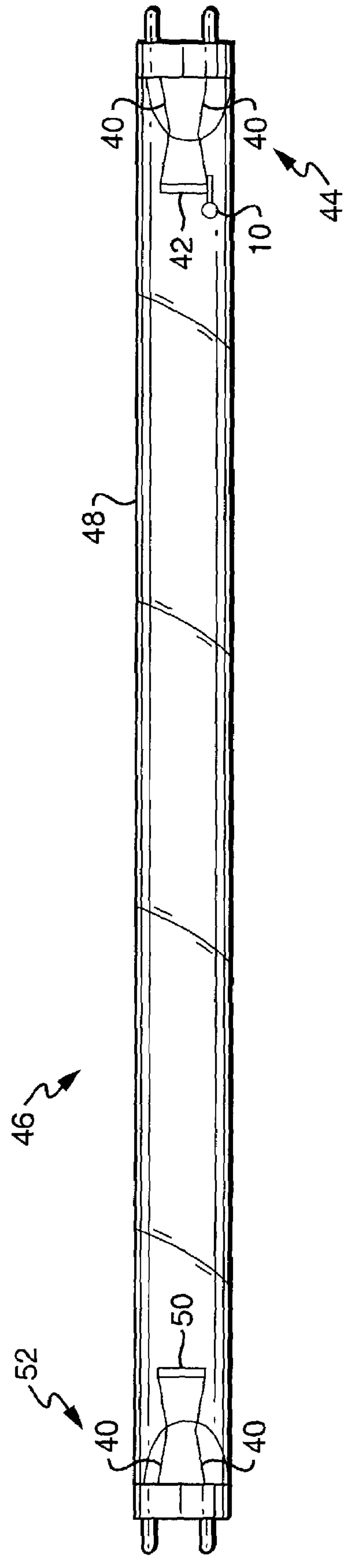
FIG. 3 is a diagrammatic elevational view of an embodiment of the invention mounted in a fluorescent lamp.

Upon completion of the dispenser 10 or 10*a* it is ready for insertion into a desired environment. When that environment is the interior of a fluorescent lamp (see FIG. 3), the dispenser 10 or 10*a* can be attached to a lead-in wire 40 of a first electrode assembly 42. Electrode assembly 42 is then fixed in a first end 44 of a fluorescent lamp 46, defined in relevant part by an envelope 48 of a vitreous material. A second electrode assembly 50 is fixed in a second end 52. The envelope 48 is filled with an inert gas, as is known in the art. In the finished lamp, rupture of the dispenser is caused by the application of heat via the application of RF.

Figure 5:
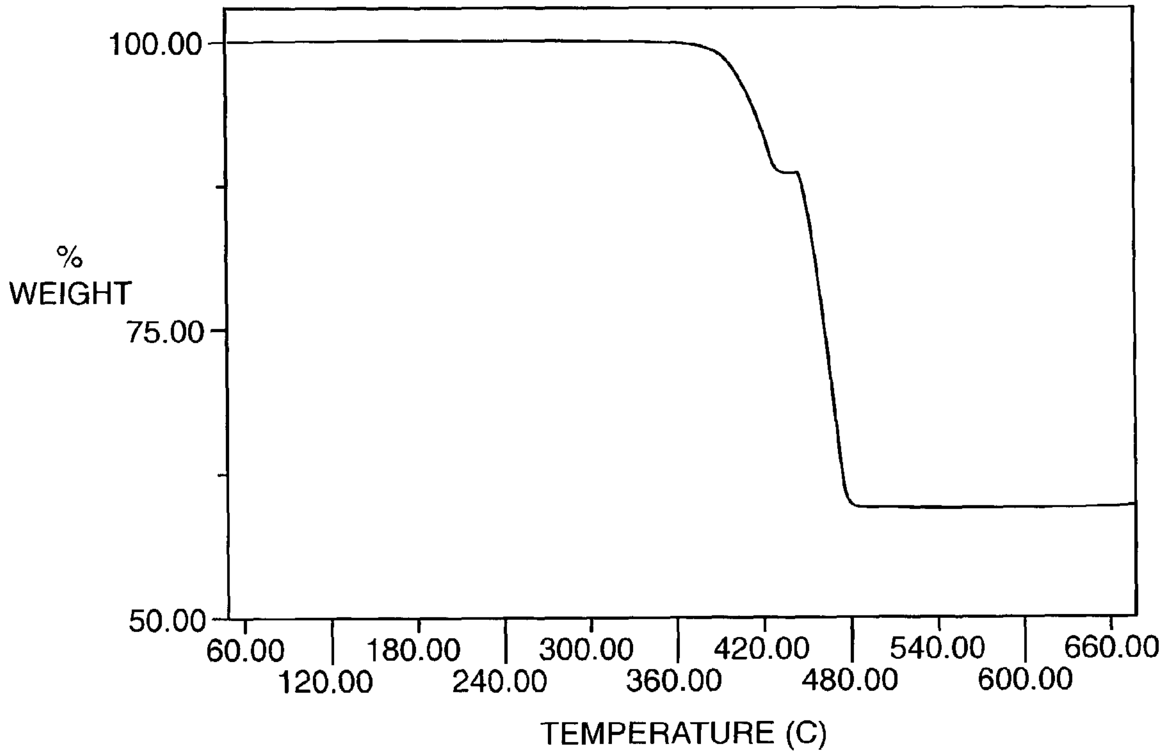
FIG. 5 is a graph of mercury release in dispensers without an hermetic seal.

During the assembly of the fluorescent lamp 46 temperatures up to 400° C. are encountered and it is important that mercury (when it is the volatilizable material) not be released during this period. However, tests have shown that when the dispensers are formed with two nested members, having no additional sealing, mercury release often occurs at improper times. FIG. 5 graphically illustrates this problem. The results of the tests shown in FIG. 5 were achieved by heating non-hermetically sealed nested members (as available from the prior art) on a microbalance, i.e., a thermogravimetric analysis system (hereinafter, TGA). As is apparent from the rounded shoulder of the graph of FIG. 5, mercury release starts occurring at about 370° C. and is essentially completed at about 480° C.

Figure 6:
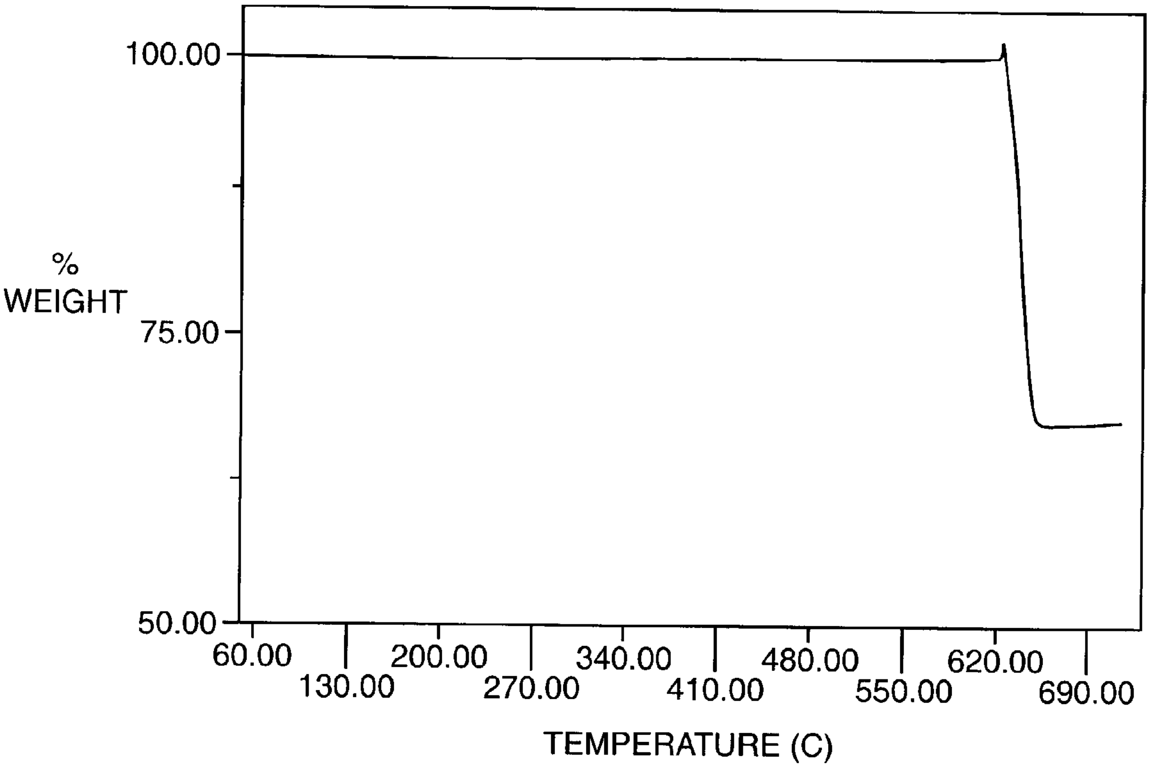
FIG. 6 is a graph of mercury release in dispensers with an hermetic seal made in accordance with an aspect of the invention.

In contrast, the graph of FIG. 6 illustrates the test results with dispensers having the hermetic seal disclosed herein. The sudden weight change at about 600° C. indicates the sudden release of mercury through the seal at the desired temperature.

In preferred embodiments of the invention the material employed for the dispensers can be steel, stainless steel, nickel-plated stainless steel or nickel The material can have a thickness of about 0.0060 inches and the diameter of the cup can be about 0.088 inches. The depth of the cup will be determined by the volume necessary to accommodate the desired amount of volatilizable material, but can be in the neighborhood of 0.080 inches.

The annular bosses 64, 66 on tools 60 and 62 can have a height of 0.006 inches; however, this height will be dependent, of course, on the thickness and hardness of the material being employed for the dispensers.

There is thus provided a volatilizable material dispenser having a suitable temperature release control for admitting the volatilizable material into a desirable environment, specifically, the interior of a fluorescent lamp envelope.

While there have been shown and described what are at present considered to be the preferred embodiments of the invention, it will be apparent to those skilled in the art that various changes and modification can be made herein without departing from the scope of the invention as defined by the appended claims.

What is claimed is:

1. A dispenser for a volatilizable material comprising: a first member that is substantially cup-shaped having a given diameter and with a given depth and having a first peripheral flange having a first diameter; a second member having a second peripheral flange having a second diameter greater than said given diameter, said first peripheral flange and said second peripheral flange being in intimate contact thereby defining a volatilizable material chamber between the bottom of said second member and the bottom of said first cup-shaped member; a volatilizable material in said chamber; and a hermetic seal formed between said first and second flanges, said hermetic seal constructed to rupture when pressure within said volatilizable chamber reaches about 20 atmospheres, thereby releasing said volatilizable material into a desirable environment.

2. The dispenser of claim 1 wherein said hermetic seal comprises a ring seal.

3. The dispenser of claim 1 wherein the material for said dispenser is selected from the group of steel, stainless steel, nickel-plated stainless steel and nickel.

4. A dispenser for a volatilizable material comprising: a first member that is substantially cup-shaped with a given depth and having a first peripheral flange; a second member that is substantially cup-shaped having a second depth less than said first depth and having a second peripheral flange, said second member being nested within said first member and defining a volatilizable material chamber between the bottom of said second member and the bottom of said first member, said first peripheral flange and said second peripheral flange being in intimate contact; a volatilizable material in said chamber; and a hermetic seal formed between said first and second flanges, said hermetic seal constructed to rupture when pressure within said volatilizable chamber reaches about 20 atmospheres, thereby releasing said volatilizable material into a desirable environment.

5. The dispenser of claim 4 wherein said hermetic seal comprises a ring seal.

6. The dispenser of claim 4 wherein the material for said dispenser is selected from the group of steel, stainless steel nickel-plated stainless steel and nickel.

7. A method of releasing a volatilizable material into a desirable environment comprising the steps of: forming a first member having a chamber to receive a volatilizable material, and a first peripheral flange; forming a second member having a second peripheral flange to serve as cover for said first member; placing a volatilizable material within said chamber; forming a hermetical seal between said first and second flanges to form a sealed dispenser; securing said sealed dispenser within said desirable environment; and heating said dispenser until the vapor pressure in said chamber is sufficiently high to rupture said hermetic seal between said first and second flanges and release said volatilizable material into said desirable environment.

8. The method of claim 7 wherein said vapor pressure upon said heating is about 20 atmospheres.

* * * * *